United States Patent
Ley

(10) Patent No.: US 6,265,611 B1
(45) Date of Patent: Jul. 24, 2001

(54) HYDROXYMANDELIC ACID AMIDES OF PHENOLIC AMINES

(75) Inventor: Jakob Peter Ley, Holzminden (DE)

(73) Assignee: Haarmann & Reimer GmbH, Holzminden (DE)

( * ) Notice: Subject to any disclaimer, the term of this patent is extended or adjusted under 35 U.S.C. 154(b) by 0 days.

(21) Appl. No.: 09/502,128

(22) Filed: Feb. 10, 2000

(30) Foreign Application Priority Data

Feb. 19, 1999 (DE) ................................. 199 07 032
Jul. 12, 1999 (DE) ................................. 199 32 491

(51) Int. Cl.$^7$ ................ C07C 233/05; A61K 31/165; C09K 15/16
(52) U.S. Cl. ............... 564/170; 252/399; 252/401; 252/404; 426/442; 426/546; 514/617; 564/139; 564/142
(58) Field of Search ............... 564/170, 139, 564/142; 514/617; 252/401, 399, 404; 426/442, 546

(56) References Cited

U.S. PATENT DOCUMENTS 5,183,828  2/1993  Van't Reit et al. ............... 514/508

OTHER PUBLICATIONS

Barrett et al, J.C.S. Perkin I, pp 652–661, 1979.*
Teitel et al, J. Het. Chem., vol. 5, pp 825–829, 1968.*
Negrel et al, Phytochemistry, vol. 43, pp 1195–1199, 1996.*

* cited by examiner

Primary Examiner—Shailendra Kumar
(74) Attorney, Agent, or Firm—Joseph C. Gil; Noland J. Cheung

(57) ABSTRACT

The present invention relates to hydroxymandelic acid amides of phenolic amines which can be used as antioxidants or as free-radical scavengers, particularly in the cosmetic or dermatological field, in foods and in cosmetic and dermatological compositions.

12 Claims, No Drawings

HYDROXYMANDELIC ACID AMIDES OF PHENOLIC AMINES

FIELD OF THE INVENTION

The invention relates to hydroxymandelic acid amides of phenolic amines, to a process for their preparation and to their use as antioxidants or free-radical scavengers, in particular, in cosmetic and pharmaceutical preparations and foods, and for protecting cells and tissue of mammals from the harmful effects of free radicals and reactive oxygen compounds which accelerate aging. The invention further relates to cosmetic and pharmaceutical preparations comprising such hydroxymandelic acid amides.

BACKGROUND OF THE INVENTION

It is desirable to find substances, which support the natural defense mechanisms in physiological systems against free radicals and reactive oxygen compounds or, in the form of protectants in cosmetics, pharmaceuticals or foods, protect their oxidation-sensitive constituents against autoxidation.

Antioxidants are substances which, in concentrations which are small compared with the oxidizable substrate, significantly delay oxidation, or prevent it completely. Many antioxidants also act as free-radical scavengers and/or as complexing agents for heavy metal ions.

The object of the present invention is to develop new antioxidants having a high specific free-radical-scavenging and/or antioxidative action.

SUMMARY OF THE INVENTION

The invention relates to hydroxymandelic acid amides of phenolic amines, their stereoilsomers or mixtures thereof, comprising the general formula I,

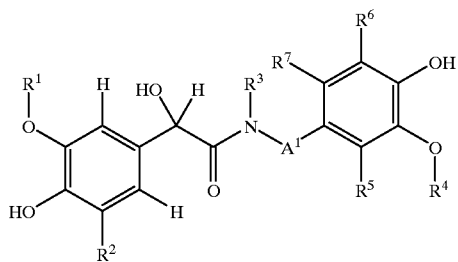

(I)

wherein
$R^1$ is a hydrogen atom or an alkyl radical having from 1 to 4 carbon atoms;
$R^2$ is a hydrogen atom or an —O—$R^8$ group, in which $R^8$ is a hydrogen atom or an alkyl radical having from 1 to 4 carbon atoms;
$R^3$ is a hydrogen atom, an acyl, alkyl or alkenyl radical having from 1 to 22 carbon atoms;
$A^1$ is a —$CH_2$— group or a —$CH_2$—$CH_2$— group;
$R^4$ is a hydrogen atom or an alkyl radical having from 1 to 4 carbon atoms; and
$R^5$, $R^6$ and $R^7$ independently of one another are hydrogen atoms or —O—$R^9$ groups, where $R^9$ is a hydrogen atom or an alkyl radical having from 1 to 4 carbon atoms.

DETAILED DESCRIPTION OF THE INVENTION

Preference is given to compounds of the general formula I
wherein
$R^1$ is a hydrogen atom or a methyl group;
$R^2$ is a hydrogen atom, a hydroxyl group or an —O—$CH_3$ group;
$R^3$ is a hydrogen atom;
$A^1$ is a —$CH_2$— group or a —$CH_2$—$CH_2$— group;
$R^4$ is a hydrogen atom or a methyl group, and
$R^5$, $R^6$ and $R^7$ independently of one another are hydrogen atoms, hydroxyl groups or —O—$CH_3$ groups.

Particular preference is given to compounds in which $A^1$ is a —$CH_2$— group.

The particularly preferred compounds of the general formula (I) include, for example:
N-(3,4-dihydroxyphenethyl)-2-hydroxy-2-(4-hydroxy-3-methoxyphenyl)acetamide;
N-(3,4-dihydroxyphenethyl)-2-(3,4-dihydroxyphenyl)-2-hydroxyacetamide;
N-(3,4-dihydroxybenzyl)-2-hydroxy-2-(4-hydroxy-3-methoxyphenyl)acetamide;
2-hydroxy-2-(4-hydroxy-3-methoxyphenyl)-N-(3,4,5-trihydroxybenzyl)acetamide;
2-(3,4-dihydroxyphenyl)-2-hydroxy-N-(4-hydroxy-3-methoxybenzyl)acetamide;
N-(3,4-dihydroxybenzyl)-2-(3,4-dihydroxyphenyl)-2-hydroxyacetamide;
2-(3,4-dihydroxyphenyl)-2-hydroxy-N-(3,4,5-trihydroxybenzyl)acetamide;
but are not limited thereto.

Surprisingly, we have now found that the hydroxymandelic acid amides of phenolic amines according to the present invention are particularly strong free-radical scavengers and antioxidants. In particular, they are significantly better antioxidants and free-radical scavengers than most customary antioxidants.

Compared to phenolic acid amides of hydroxyl-substituted benzylamines known from EP 0 900 781, the hydroxymandelic acid amides of phenolic amines according to the present invention have increased water solubility, meaning that they can be used more easily in cosmetic preparations.

Particularly advantageous antioxidants or free-radical scavengers are the compounds within the meaning of the invention having more than two hydroxyl groups.

The hydroxymandelic acid amides of phenolic amines according to the present invention and of the general formula I can be prepared using the customary amide synthesis processes known per se, by reacting an activated hydroxymandelic acid, optionally protected on the OH groups, with a phenolic amine, optionally protected on the phenolic OH groups, or its ammonium salt, optionally in the presence of solvents and auxiliary bases. Activated acid derivatives which may be used are the acid chlorides, the acid anhydrides or acid esters of, for example, optionally substituted phenols, N-hydroxysuccinimide or N-hydroxybenzotriazole. The protective groups are preferably acyl, carbamate or ether groups, e.g. acetyl, benzoyl, methoxycarbonyl, tert-butoxycarbonyl, allyl or benzyl groups. Solvents which can be used are, for example, water, acetone, 1,4-dioxane, N,N-dimethylformamide, tetrahydrofuran, ethyl acetate, chloroform or else mixtures of the last-named solvents. Auxiliary bases which can be used are, for example, the carbonates, hydrogencarbonates and hydroxides of ammonium, alkali metals or alkaline earth metals, tertiary amines, and inorganic or organic basic ion exchangers.

The hydroxymandelic acid amides of phenolic amines according to the present invention and of the general formula I are particularly preferably prepared from N-succinimidyl hydroxy mandelates, optionally blocked on the hydroxyl groups with acetyl or methoxycarbonyl groups, with a phenolic amine or its ammonium salt in a hydrosolvent mixture, preferably a water/1,4-dioxane mixture with one of the above-mentioned auxiliary bases at from 5 to 100° C. Advantageously, the N-succinimidyl hydroxymandelate, optionally blocked on the hydroxyl groups with acetyl or methoxycarbonyl groups, are synthesized from the corresponding free acid and N-hydroxysuccinimide using a carbodiimide, preferably N,N'-dicyclohexylcarbodiimide, in an aprotic solvent, preferably 1,4-dioxane, diethyl ether, tert-butyl methyl ether, ethyl acetate or tetra-hydrofuran, at from 0 to 50° C., preferably from 5 to 30° C., the dissolved crude product is separated from the residue by filtration, and the filtrate is reacted directly within the meaning of the invention with the phenolic amine, initially introduced into water, or its ammonium salt and one of the above-mentioned auxiliary bases.

The hydroxymandelic acids are, in particular, 2-(4-hydroxy-3-methoxyphenyl)-2-hydroxyacetic acid (vanillomandelic acid) and 2-(3,4-dihydroxyphenyl)-2-hydroxyacetic acid (3,4-dihydroxymandelic acid) and their stereoisomers or mixtures.

The phenolic amines are, in particular, 2-(3,4-dihydroxyphenyl)-ethylamine, 3,4-dihydroxybenzylamine, 4-hydroxy-3-methoxybenzylamine or 3,4,5-trihydroxybenzylamine or the respective ammonium salts.

The hydroxymandelic acid amides according to the present invention can, however, also be obtained by direct condensation of the free acids with the free amines with or without solvent. Condensing agents which may be used are, for example, carbodiimides, preferably N,N'-dicyclohexylcarbodiimide, and solvents which may be used are, for example, 1,4-dioxane, diethyl ether, tert-butyl methyl ether, ethyl acetate or tetrahydrofuran.

The hydroxymandelic acid amides of phenolic amines according to the present invention are obtained from these reaction mixtures by purification stages known per se; if necessary, any protective groups which are present must be cleaved off using methods known per se.

The hydroxymandelic acid amides of phenolic amines according to the present invention and of the general formula I, their stereoisomers and mixtures thereof can be used as antioxidants or free-radical scavengers for protecting against oxidation and photooxidation. They can be used preferably in cosmetic, pharmaceutical or dermatological formulations or in foods. Particularly preferably, the hydroxy-mandelic acid amides of phenolic amines according to the present invention are used in cosmetic and dermatological formulations, which have the customary composition and are used for the treatment, protection, care and cleansing of the skin, of the nails and/or of the hair and as make-up products in decorative cosmetics.

Accordingly, the present invention also relates to cosmetic and pharmaceutical compositions, in particular, cosmetic and dermatological compositions which comprise the hydroxymandelic acid amides of phenolic amines according to the present invention in an effective amount alongside other, otherwise customary composition constituents. They comprise from 0.0001% by weight to 30% by weight, preferably from 0.0001 to 20% by weight, but, in particular, from 0.0001% by weight to 5% by weight, based on the total weight of the formulation, of the hydroxy-mandelic acid amides of phenolic amines according to the present invention and of the general formula I and can be in the form of "water-in-oil", "oil-in-water", "water-in-oil-in-water" or "oil-in-water-in-oil" emulsions, gels, solutions e.g., in oils, alcohols or silicone oils, sticks, aerosols, sprays or else foams. Other customary cosmetic auxiliaries and additives can be present in amounts of 5–95% by weight, preferably 10–80% by weight, based on the total weight of the formulation. In addition, the formulations can comprise water in an amount up to 99% by weight, preferably 5–80% by weight, based on the total weight of the formulation.

For use, the cosmetic and dermatological preparations according to the present invention are applied to the skin and/or the hair in a sufficient amount in the manner customary for cosmetics.

The cosmetic and dermatological preparations according to the present invention can comprise cosmetic auxiliaries and additives, as are customarily-used in such preparations, e.g., preservatives, bactericides, fungicides, virucides, light filter substances, active ingredients with a cooling action, plant extracts, antiinflammatories, substances which promote wound healing, skin-lightening agents, skin-coloring agents, perfumes, antifoams, dyes, pigments which have a coloring action, thickeners, surface-active substances, emulsifiers, emollients, moisturizers and/or humectants, fats, oils, waxes or other customary constituents of a cosmetic or dermatological formulation, such as alcohols, polyols, polymers, foam stabilizers, electrolytes, organic solvents, silicone derivatives or chelating agents.

Preferably, the hydroxymandelic acid amides of phenolic amines according to the present invention can be combined with one another or with other antioxidants. In particular, the hydroxymandelic acid amides of phenolic amines according to the present invention can be combined with one another and also with tocopherols (vitamin E), tocopherol derivatives, tocotrienols, ascorbic acid (vitamin C), ascorbic acid derivatives, carotenoids, vitamin A or derivatives thereof, butylated hydroxytoluene, butylated hydroxyanisole, gallic esters, flavonoids such as, for example, quercetin or myricetin, catechins such as, for example, epicatechin, epicatechingallate, epigallocatechin or epigallocatechingallate, sulfur-containing molecules such as, for example, glutathione, cysteine, lipoic acid, N-acetylcystein, chelating agents such as, for example, ethylenediamine tetraacetic acid or other customary antioxidants.

In the preparations according to the present invention, the amount of the above-illustrative antioxidants (one or more compounds), which are not identical to the hydroxymandelic acid amides of phenolic amines according to the present invention, can be from 0.0001 to 30% by weight, preferably from 0.0001 to 20% by weight, particularly preferably from 0.0001 to 5% by weight, based on the total weight of the preparation.

The hydroxymandelic acid amides of phenolic amines according to the present invention can, however, also be used together with WVA and/or UVB filter substances in the cosmetic or dermatological formulations according to the present invention, wherein the total amount of filter substances can be from 0.1 to 30% by weight, preferably from 0.5 to 10% by weight, based on the total weight of the preparations, giving sunscreens for skin and hair. Examples of UV filter substances which may be used are 3-benzylidenecamphor derivatives, e.g. 3-(4-methylbenzylidene)-dl-camphor, aminobenzoic acid derivatives, e.g. 2-ethylhexyl 4-(N,N-dimethylamino)benzoate or menthyl anthranilate, 4-methoxy-cinnamates, e.g., 2-ethylhexyl p-methoxycinnamate or isoamyl p-methoxycinnamate, benzophenones, e.g., 2-hydroxy-4-methoxybenzophenone, sulfonated UV filters, e.g., 2-phenylbenzamidizole-5-sulphonic acid or 1,4-bis(benzimidazolyl)-benzene-4,4',6,6'-tetrasulphonic acid or sodium salts thereof, salicylates, e.g. 2-ethylhexyl salicylates, triazines, e.g., octyltriazone, 2-cyanopropenoic derivative, e.g., 2-ethylhexyl 2-cyano-3,3-diphenyl-2-propenoate, dibenzoyl derivatives, e.g., 4-tert-butyl-4'-methoxydibenzoylmethane or pigments, e.g., titanium dioxides, zirconium dioxides, iron oxides, silicone dioxides, manganese oxides, aluminum oxides, cerium oxides or zinc oxides.

Finally, in a preferred embodiment, the hydroxymandelic acid amides of phenolic amines within the meaning of the present invention can also be dissolved in squalene or squalane and, if appropriate, be formulated with the other ingredients together with volatile or nonvolatile silicone compounds as anhydrous or virtually anhydrous systems.

An advantageous embodiment of the present invention is regarded as the use of the hydroxymandelic acid amides of phenolic amines according to the present invention for the protection of tissues and cells of mammals, in particular of the skin and/or of the hair, against oxidative stress and the harmful effect of free radicals.

Likewise, the present invention also includes a process for protecting cosmetic or dermatological preparations from oxidation or photooxidation, where these preparations are, for example, preparations for the treatment, protection and care of the skin, of the nails or of the hair or, in addition, also make-up products, the constituents of which have stability problems during storage because of oxidation or photooxidation, characterized in that the cosmetic or dermatological preparations have an effective content of hydroxymandelic acid amides of phenolic amines according to the present invention.

The hydroxymandelic acid amides of phenolic amines according to the present invention can, thus, also be used for the preparation of pharmaceutical, in particular, of dermatological, compositions for protecting cells and tissues of mammals, in particular of man, from the harmful effect of free radicals and reactive oxygen species.

The amount of hydroxymandelic acid amides of phenolic amines according to the present invention in these preparations is from 0.0001% by weight to 30% by weight, preferably from 0.0001 to 20% by weight, and particularly preferably from 0.0001% by weight to 5% by weight, based on the total weight of the preparations.

The present invention also includes the use of the hydroxymandelic acid amides of phenolic amines according to the present invention for the protection of foods, preferably foods containing fats or fat derivatives such as, for example, fatty acids or fatty alcohols, but in particular, foods which contain fats or fatty derivatives having oxidizable double bonds, from oxidative stress and from the harmful effect of free radicals.

The amount of hydroxymandelic acid amides of phenolic amines according to the present invention in foods is preferably from 0.0001% by weight to 30% by weight, particularly preferably from 0.0001 to 20% by weight, but in particular from 0.0001% by weight to 5% by weight, based on the total weight of the food.

For the use according to the present invention for protecting foods, the hydroxy-mandelic acid amides of phenolic amines according to the present invention can preferably be combined with one another and also with other antioxidants, examples of which are listed above.

The amount of the above-mentioned illustrative antioxidants (one or more compounds) which are not identical to the hydroxymandelic acid amides of phenolic amines according to the present invention in the foods is from 0.0001 to 30% by weight, preferably from 0.0001 to 20% by weight, particularly preferably from 0.0001 to 5% by weight, based on the total weight of the food.

The invention is further illustrated but is not intended to be limited by the following examples in which all parts and percentages are by weight unless otherwise specified.

EXAMPLES

The examples below serve to illustrate the present invention without in any way limiting the invention.

Example 1

N-(3,4-dihydroxyphenethyl)-2-hydroxy-2-(4-hydroxy-3 methoxyphenyl)acetamide 2-(4-Hydroxy-3-methoxyphenyl)-2-hydroxyacetic acid (2 g, 10:1 mmol) and N-hydroxysuccinimide (1.16 g, 10.1 mmol) were dissolved in 1,4-dioxane (120 ml) under nitrogen. N,N'-dicyclohexylcarbodiimide (2.08 g, 0.1 mmol) was added to the mixture at room temperature, and the mixture was stirred at this temperature for 48 h. The by-product which precipitated out was filtered off, and the filtrate was evaporated under reduced pressure. The product was chromatographed on silica gel with the eluent ethyl acetate. The yield was 1.72 g (58%). A solution of 2-(3,4-dihydroxyphenyl)-ethylamine hydrochloride (385 mg, 2.03 mmol) in water (30 ml) was added to a solution of the product (500 mg, 1.69 mmol) in 30 ml of 1,4-dioxane under nitrogen, followed by sodium hydrogencarbonate (142 mg, 1.69 mmol). The mixture was stirred at 50° C. for 4 h, then rendered acidic using 10% strength hydrochloric acid, and the reaction solution was extracted 3 times with ethyl acetate (a total of 90 ml). The organic phase was washed with saturated NaCl solution, dried over $Na_2SO_4$ and filtered, and the filtrate was evaporated under reduced pressure. Purification was carried out by chromatography on silica gel using the eluent ethyl acetate. The yield was 231 mg of an amorphous, colorless solid (41% of theory).

$^1$H-NMR (400 MHz, $CD_3OD$ with water suppression): δ=6.94 (1H, d 1.9 Hz), 6.79 (1H, ddd, 8 Hz, 2 Hz, 0.5 Hz), 6.74 (1H), d, 8.1 Hz), 6.654 (1H, d, 7.9 Hz), 6.647 (1H, d, 2 Hz), 6.48 (1H), dd, 8.1 Hz, 1.9 Hz), 4.87 (partially suppressed, s), 3.82 (3H, s), 3.46–3.36 (2H, m), 2.68–2.63 (2H, m) ppm; $^{13}$C-NMR (100 MHz, CD$_3$OD): δ=175.7 (C), 149.0 (C), 133.1 (C), 131.8 (C), 121.0 (2×CH), 116.8 (CH), 116.4 (CH), 116.1 (CH), 111.6 (CH), 75.5 (CH), 56.4 (CH$_3$), 41.8 (CH$_2$), 35.9 (CH$_2$) ppm; MS (CI-): m/e=332.1 (100%, [M-H]$^-$), 664.6 (17%, [2M-H]).

Example 2

N-(3,4-dihydroxyphenethyl)-2-(3,4-dihydroxyphenyl)-2-hydroxyacetamide 2-(3,4-Dihydroxyphenyl)-2-hydroxyacetic acid (300 mg, 1.63 mmol) and N-hydroxysuccinimide (188 mg, 1.63 mmol) were dissolved in 1,4-dioxane (20 ml) under nitrogen, and N,N'-dicyclohexylcarbodiimide (336 mg, 1.63 mmol) was added to the mixture at room temperature, which was stirred at this temperature for 16 h. The by-product which precipitated out was filtered off, and the filtrate was added to a solution of 2-(3,4-dihydroxyphenyl)ethylamine hydrochloride (309 mg, 1.63 mmol) in water (20 ml). Sodium hydrogencarbonate (151 mg, 1.8 mmol) was also added, and the reaction mixture was stirred under nitrogen at 50° C. for 1.5 h. The mixture was rendered acidic using 5% strength hydrochloric acid and extracted 3 times with ethyl acetate (a total of 90 ml). The organic phase was washed with saturated NaCl solution, dried over Na$_2$SO$_4$ and filtered, and the filtrate was evaporated under reduced pressure. The product was purified by chromatography on silica gel using the eluent ethyl acetate. The yield was 266 mg of a colorless syrup (51% of theory based on the acid used).

$^1$H-NMR (400 MHz, CD$_3$OD with water suppression): δ=6.83 (1H, d, 2 Hz), 6.72 (1H, d, 8 Hz), 6.674 (1H, ddd, 8 Hz, 2 Hz, 0.5 Hz), 6.672 (1H, d, 8 Hz), 6.65 (1H, d, 2 Hz), 6.50 (1H, dd, 8 Hz, 2.1 Hz), 3.43–3.35 (2H, m), 2.65 (t, 7.6 Hz) ppm; $^3$C-NMR (100 MHz, CD$_3$OD): δ=175.8 (C), 146.5 (C), 146.3 (C), 146.26 (C), 144.9 (C), 133.3 (C), 131.9 (C), 121.2 (CH), 119.9 (CH), 116.9 (CH), 116.5 (CH), 116.2 (CH), 115.4 (CH), 75.4 (CH), 41.9 (CH$_2$), 36.0 (CH$_2$) ppm; MS (CI-): m/e=318.8 (100%, [M-H]$^-$), 636.4 (23%, [2M-H]$^-$).

The compounds below were obtained in an analogous manner in the form of colorless or slightly yellowish amorphous solids:

Example 3

N-(3,4-dihydroxybenzyl)-2-hydroxy-2-(4-hydroxy-3methoxyphenyl)acetamide $^1$H-NMR (400 MHz, CD$_3$OD with water suppression): δ=6.94 (1H, d, 2.1 Hz), 6.87 (1H, ddd, 8.1 Hz, 2.0 Hz, 0.5 Hz), 6.75 (1H, d, 8.1 Hz), 6.73 (1H, d, 2.0 Hz), 6.68 (1H, d, 8.0 Hz), 6.60 (1H, ddd, 8.0 Hz, 2.1 Hz, 0.6 Hz), 4.94 (partially suppressed, s), 4.32 (1H, d, 14.5 Hz), 4.21 (1H, d, 14.5 Hz), 3.78 (3H, s) ppm; $^{13}$C-NMR (100 MHz, CD$_3$OD): δ=175.5 (C), 149.0 (C), 147.7 (C), 146.4 (C), 145.7 (C), 133.3 (C), 131.6 (C), 121.3 (CH), 120.3 (CH), 116.3 (CH), 116.1 (CH), 115.9 (CH), 111.4 (CH), 75.5 (CH), 56.4 (CH$_3$), 43.5 (CH$_2$) ppm; MS (CI-): m/e=318.1 (100%, [M-H]$^-$).

Example 4

2-Hydroxy-2-(4-hydroxy-3-methoxyphenyl)-N-(3,4,5-trihydroxybenzyl)acetamide $^1$H-NMR (400 MHz, CD$_3$OD with water suppression): δ=6.93 (1H, d, 2.1 Hz), 6.86 (1H, ddd, 8.1 Hz, 2.1 Hz, 0.5 Hz), 6.75 (1H, d, 8.1 Hz), 6.31 (2H, t, 0.6 Hz), 4.93 (partially suppressed, s), 4.27 (1H, d, 14.3 Hz), 4.14 (1H, d, 14.3 Hz), 3.79 (3H, s) ppm; $^{13}$C-NMR (100 MHz, CD$_3$OD): δ=175.5 (C), 149.0 (C), 147.7 (C), 147.1 (2×C), 133.3 (C), 130.9 (C), 121.3 (CH), 116.0 (CH), 111.4 (CH), 107.9 (2×CH), 75.5 (CH), 56.4 (CH$_3$), 43.7 (CH$_2$) ppm; MS (CI-): m/e=334.0 (100%, [M-H]$^-$), 668.7 (5%, [2M-H]$^-$).

Example 5

2-(3,4-Dihydroxyphenyl)-2-hydroxy-N-(4-hydroxy-3 methoxybenzyl)acetamide $^1$H-NMR (400 MHz, CD$_3$OD with water suppression): δ=6.90 (1H, dt, 2.1 Hz, 0.4 Hz), 6.78 (1H, ddd, 8.2 Hz, 2.1 Hz, 0.6 Hz), 6.74 (1H, d, 1.6 Hz), 6.72 (1H, d, 8.2 Hz), 6.71 (1H, dd, 8.0 Hz, 0.4 Hz), 6.68 (1H, dd, 8.0 Hz, 1.8 Hz), 4.90 (partially suppressed, s), 4.36 (1H, d, 14.7 Hz), 4.28 (1H, d, 14.7 Hz), 3.73 (3H, d, 0.4 Hz) ppm; $^{13}$C-NMR (100 MHz, CD$_3$OD): δ=175.8 (C), 149.1 (C), 146.7 (C), 146.5 (C), 146.4 (C), 133.4 (C), 131.5 (C), 121.1 (CH), 119.7 (CH), 116.1 (CH), 116.0 (CH), 115.1 (CH), 112.0 (CH), 75.4 (CH), 56.3 (CH$_3$), 43.4 (CH$_2$) ppm; MS (CI-): m/e=318.0 (100%, [M-H]$^-$), 301.7 (22%), 300.5 (34%).

Example 6

N-(3,4-dihydroxybenzyl)-2-(3,4-dihydroxyphenyl)-2-hydroxyacetamide $^1$H-NMR (400 MHz, CD$_3$OD with water suppression): δ=6.87 (1H, dt, 1.9 Hz, 0.5 Hz), 6.75 (1H, ddd, 8.1 Hz, 1.9 Hz, 0.5 Hz), 6.72 (1H, dd, 8.1 Hz, 0.5 Hz), 6.72 (1H, dm, 2.1 Hz, 0.3 Hz), 6.69 (1H, d, 8.0 Hz), 6.59 (1H, ddt, 8.0 Hz, 2.1 Hz, 0.6 Hz), 4.88 (partially suppressed, s), 4.25 (2H, s), ppm; $^{13}$C-NMR (100 MHz, CD$_3$OD): δ=175.6 (C), 146.6 (C), 146.5 (C), 146.4 (C), 145.8 (C), 133.2 (C), 131.3 (C), 120.2 (CH), 119.8 (CH), 116.3 (CH), 116.1 (CH), 116.0 (CH), 115.3 (CH), 75.4 (CH), 43.6 (CH$_2$) ppm; MS (CI-): m/e=304.1 (10%, [M-H]$^-$), 608.7 (100%, [2M-H]$^-$).

Example 7

2-(3,4-Dihydroxyphenyl)-2-hydroxy-N-(3,4,5-trihydroxybenzyl)acetamide $^1$H-NMR (400 MHz, CD$_3$OD with water suppression): δ=6.86 (1H, dt, 2.0 Hz, 0.5 Hz), 6.75 (1H, ddd, 8.1 Hz, 2.0 Hz, 0.5 Hz), 6.72 (1H, dd, 8.1 Hz, 0.5 Hz), 6.30 (2H, t, 0.5 Hz), 4.88 (partially suppressed, s), 4.20 (2H, s) ppm; $^{13}$C-NMR (100 MHz, CD$_3$OD): δ=175.5 (C), 147.1 (2×C), 146.5 (C), 146.3 (C), 133.3 (C), 130.7 (C), 119.9 (CH), 116.2 (CH), 115.4 (CH), 107.8 (2×CH), 75.4 (CH), 43,8 (CH$_2$) ppm; MS (CI-): m/e=320.8 (100%, [M-H]$^-$), 641.0 (100%, [2M-H]$^-$).

Example 8

Activity as Free-radical Scavenger

The activity of the compounds according to Examples 1 to 7 as free-radical scavengers was compared with the conventional free-radical scavenger. For this purpose, the DPPH (1,1-diphenyl-2-picryl-hydrazyl) test for the removal of free-radical scavengers was used.

DPPH was dissolved in methanol to a concentration of 100 μmol/l. A series of dilutions of the illustrative compound, vitamin C, α tocopherol, butylated hydroxytoluene and ferulic acid in methanol were prepared. Methanol was used as the control. 2500 μl of the DPPH solution were mixed with 500 μl of each test solution and the decrease in absorption at 515 nm was read until the decrease was less than 2% per hour. The activity of the test substances as free-radical scavengers was calculated using the following equation:

Activity as free-radical scavenger (%)=100−(absorption of the test compounds)/ (absorption of the control)×100.

The activity of the free-radical scavengers (%) in a series of dilutions of test compounds was used to calculate, for each test compound, the effective relative concentration $EC_{50}$ (based on the starting concentration of DPPH, EC=c (test compound)/c(DPPH)) of a test compound at which 50% of the free radical DPPH had been removed. The results are given in Table 1:

TABLE 1

| Test compound | $EC_{50}$/(mol/mol) |
|---|---|
| Example 1 | 0.131 |
| Example 2 | 0.104 |
| Example 3 | 0.195 |
| Example 4 | 0.198 |
| Example 5 | 0.199 |
| Example 6 | 0.069 |
| Example 7 | 0.085 |
| Vitamin C | 0.270 |
| α-Tocopherol | 0.250 |
| Ferulic acid | 0.350 |
| Butylated hydroxytoluene | 0.240 |

Example 9

Activity as Antioxidants

The activity of the illustrative compounds 1 to 7 as antioxidants was compared with that of traditional antioxidants. The test system used was the accelerated autoxidation of lipids by air with or without antioxidant using the Rancimat apparatus (Rancimat is a registered trade mark of Metrohm AG, Herisau, Switzerland).

The illustrative compounds, vitamin C, α-tocopherol, ferulic acid and butylated hydroxytoluene were dissolved in methanol or acetone, and 100 μl of each test solution were added to a 3 g prepared oil sample (soybean oil, purified over alumina type N). In a control sample, only solvent was added. A constant, dry stream of air (20 l/h) was blown through the oil sample, which contained the test solution and was heated to 100° C., and the volatile oxidation product (predominantly short-chain fatty acids such as formic or acetic acid) were collected in a trap containing water. The conductivity of this aqueous solution was continuously measured and recorded. The oxidation of (unsaturated) fats proceeded only very slowly for some time and then suddenly increased. The time to the increase is referred to as the induction period (IP).

The following equation was used to calculate the antioxidative index (AOI):

$$AOI = IP_{(with\ test\ solution)} / IP_{(control\ sample)}$$

The results are shown in Table 2:

TABLE 2

| Test compound | AOI with 0.05% of test substance |
|---|---|
| Example 1 | 13.0 |
| Example 2 | 16.9 |
| Example 3 | 9.8 |
| Example 4 | 11.0 |
| Example 5 | 12.6 |
| Example 6 | 17.5 |
| Example 7 | 16.4 |
| Vitamin C | 1.17 |
| α-Tocopherol | 5.05 |
| Ferulic acid | 1.79 |
| Butylated hydroxytoluene | 4.77 |

Example 10

Solubility in Aqueous Media

The solubility of the illustrative compounds 1 to 7 in aqueous media was compared with that of various phenol acid amides from EP 0 900 781. The aqueous medium used by way, of example, was a mixture of 95 parts by weight of water and 5 parts by weight of DMSO. The compounds to be tested were weighed into a glass vessel, admixed with a defined amount of solvent and treated with ultrasound at room temperature for 5 min. This procedure was repeated until the compound had completely dissolved. At a solubility of <0.05% by weight, the experiment was terminated.

TABLE 3

| Test compound | Solubility in a mixture of water (95 parts by weight) and DMSO (5 parts by weight) |
|---|---|
| Example 1 | 5–10% by weight |
| Example 2 | >10% by weight |
| Example 3 | >10% by weight |
| Example 4 | 0.5 to 1% by weight |
| Example 5 | 0.05 to 0.1% by weight |
| Example 6 | 0.1 to 0.5% by weight |
| Example 7 | 0.5 to 1% by weight |
| Comparison | |
| Example 1 from EP 0 900 781 | <0.05% by weight |
| Example 5 from EP 0 900 781 | <0.05% by weight |
| Example 8 from EP 0 900 781 | <0.05% by weight |
| Example 14 from EP 0 900 781 | <0.05% by weight |
| Example 16 from EP 0 900 781 | <0.05% by weight |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Hydroxymandelic acid amides of phenolic amines, their stereoisomers or mixtures thereof, comprising the general formula (I)

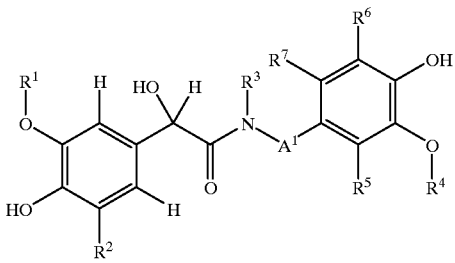

(I)

wherein
- $R^1$ is a hydrogen atom or an alkyl radical having from 1 to 4 carbon atoms;
- $R^2$ is a hydrogen atom or an —O—$R^8$ group, in which $R^8$ is a hydrogen atom or an alkyl radical having from 1 to 4 carbon atoms;
- $R^3$ is a hydrogen atom, an acyl, alkyl or alkenyl radical having from 1 to 22 carbon atoms;
- $A^1$ is a —CH$_2$— group or a —CH$_2$—CH$_2$— group;
- $R^4$ is a hydrogen atom or an alkyl radical having from 1 to 4 carbon atoms; and
- $R^5$, $R^6$ and $R^7$ independently of one another are hydrogen atoms or —O—$R^9$ groups, where $R^9$ is a hydrogen atom or an alkyl radical having from 1 to 4 carbon atoms.

2. Hydroxymandelic acid amides of the phenolic amines according to claim 1, wherein said amides are selected from the group consisting of N-(3,4-dihydroxyphenethyl)-2-hydroxy-2-(4-hydroxy-3-methoxyphenyl)acetamide; N-(3,4-dihydroxyphenethyl)-2-(3,4-dihydroxyphenyl)-2-hydroxyacetamide; N-(3,4-dihydroxybenzyl)-2-hydroxy-2-(4-hydroxy-3-methoxyphenyl)acetamide; 2-hydroxy-2-(4-hydroxy-3-methoxyphenyl)-N-(3,4,5-trihydroxybenzyl)acetamide; 2-(3,4-dihydroxyphenyl)-2-hydroxy-N-(4-hydroxy-3-methoxybenzyl)acetamide; N-(3,4-dihydroxybenzyl)-2-(3,4-dihydroxyphenyl)-2-hydroxyacetamide; and 2-(3,4-dihydroxyphenyl)-2-hydroxy-N-(3,4,5-trihydroxybenzyl)acetamide.

3. A process for the preparation of hydroxymandelic acid amides of phenolic amines, their stereoisomers or mixtures thereof comprising the general formula I,

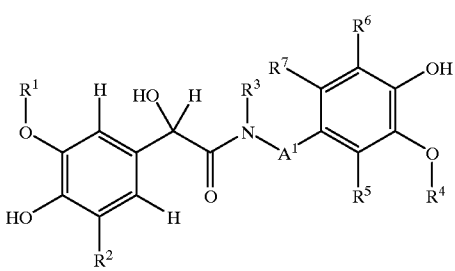

(I)

wherein
- $R^1$ is a hydrogen atom or an alkyl radical having from 1 to 4 carbon atoms;
- $R^2$ is a hydrogen atom or an —O—$R^8$ group, in which $R^8$ is a hydrogen atom or an alkyl radical having from 1 to 4 carbon atoms;
- $R^3$ is a hydrogen atom, an acyl, alkyl or alkenyl radical having from 1 to 22 carbon atoms;
- $A^1$ is a —CH$_2$— group or a —CH$_2$—CH$_2$— group;
- $R^4$ is a hydrogen atom or an alkyl radical having from 1 to 4 carbon atoms;
- $R^5$, $R^6$ and $R^7$ independently of one another are hydrogen atoms or —O—$R^9$ groups, where $R^9$ is a hydrogen atom or an alkyl radical having from 1 to 4 carbon atoms;

comprising the step of reacting an activated hydroxymandelic acid, in the form of the acid chloride, the acid anhydride or an acid ester of optionally substituted phenols, N-hydroxysuccinimide or N-hydroxybenzotriazole, and optionally protected on the phenolic OH groups, with a phenolic amine, optionally protected on the phenolic OH groups, or its ammonium salt, optionally in the presence of solvents and auxiliary bases, and cleaving off the protective groups which may be present.

4. A process according to claim 3, wherein the hydroxymandelic acids are selected from the group consisting of 2-(4-hydroxy-3-methoxyphenyl)-2-hydroxyacetic acid (vanillomandelic acid) or 2-(3,4-dihydroxyphenyl)-2-hydroxyacetic acid (3,4-dihydroxymandelic acid) and their stereoisomers or mixtures.

5. A process according to claim 3, wherein the phenolic amines are selected from the group consisting of 2-(3,4-dihydroxyphenyl)ethylamine, 3,4-dihydroxybenzylamine, 4-hydroxy-3-methoxybenzylamine or 3,4,5-trihydroxybenzylamine or the respective ammonium salts.

6. An antioxidant comprising hydroxymandelic acid amides of phenolic amines, their stereoisomers or mixtures thereof, comprising the general formula (I)

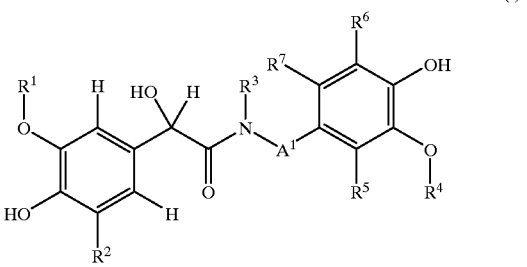

(I)

wherein
- $R^1$ is a hydrogen atom or an alkyl radical having from 1 to 4 carbon atoms;
- $R^2$ is a hydrogen atom or an —O—$R^8$ group, in which $R^8$ is a hydrogen atom or an alkyl radical having from 1 to 4 carbon atoms;
- $R^3$ is a hydrogen atom, an acyl, alkyl or alkenyl radical having from 1 to 22 carbon atoms;
- $A^1$ is a —CH$_2$— group or a —CH$_2$—CH$_2$— group;
- $R^4$ is a hydrogen atom or an alkyl radical having from 1 to 4 carbon atoms; and R$^5$, R$^6$ and R$^7$ independently of one another are hydrogen atoms or —O—R$^9$ groups, where R$^9$ is a hydrogen atom or an alkyl radical having from 1 to 4 carbon atoms.

7. A free radical scavenger comprising hydroxymandelic acid amides of phenolic amines, their stereoisomers or mixtures thereof, comprising the general formula (I)

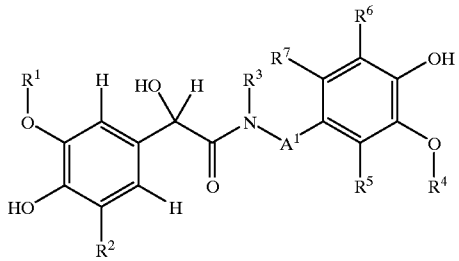

(I)

wherein

R$^1$ is a hydrogen atom or an alkyl radical having from 1 to 4 carbon atoms;

R$^2$ is a hydrogen atom or an —O—R$^8$ group, in which R$^8$ is a hydrogen atom or an alkyl radical having from 1 to 4 carbon atoms;

R$^3$ is a hydrogen atom, an acyl, alkyl or alkenyl radical having from 1 to 22 carbon atoms;

A$^1$ is a —CH$_2$— group or a —CH$_2$—CH$_2$— group;

R$^4$ is a hydrogen atom or an alkyl radical having from 1 to 4 carbon atoms; and R$^5$, R$^6$ and R$^7$ independently of one another are hydrogen atoms or —O—R$^9$ groups, where R$^9$ is a hydrogen atom or an alkyl radical having from 1 to 4 carbon atoms.

8. A cosmetic and/or pharmaceutical composition comprising at least one hydroxymandelic acid amides of phenolic, their stereoisomers or mixtures thereof, comprising the general formula (I)

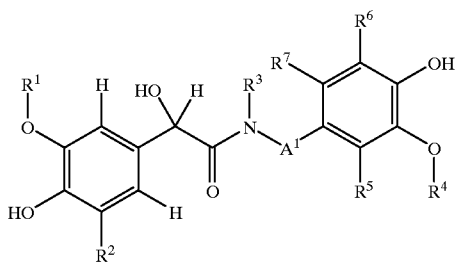

(I)

wherein

R$^1$ is a hydrogen atom or an alkyl radical having from 1 to 4 carbon atoms;

R$^2$ is a hydrogen atom or an —O—R$^8$ group, in which R$^8$ is a hydrogen atom or an alkyl radical having from 1 to 4 carbon atoms;

R$^3$ is a hydrogen atom, an acyl, alkyl or alkenyl radical having from 1 to 22 carbon atoms;

A$^1$ is a —CH$_2$— group or a —CH$_2$—CH$_2$— group;

R$^4$ is a hydrogen atom or an alkyl radical having from 1 to 4 carbon atoms; and R$^5$, R$^6$ and R$^7$ independently of one another are hydrogen atoms or —O—R$^9$ groups, where R$^9$ is a hydrogen atom or an alkyl radical having from 1 to 4 carbon atoms.

9. A cosmetic and/or pharmaceutical composition according to claim 8, wherein said amides are selected from the group consisting of N-(3,4-dihydroxyphenethyl)-2-hydroxy-2-(4-hydroxy-3-methoxyphenyl)acetamide; N-(3,4-dihydroxyphenethyl)-2-(3,4-dihydroxyphenyl)-2-hydroxy-acetamide; N-(3,4-dihydroxybenzyl)-2-hydroxy-2-(4-hydroxy-3-methoxy-phenyl)acetamide; 2-hydroxy-2-(4-hydroxy-3-methoxyphenyl)-N-(3,4,5-trihydroxybenzyl)-acetamide; 2-(3,4-dihydroxyphenyl)-2-hydroxy-N-(4-hydroxy-3-methoxybenzyl)acetamide; N-(3,4-dihydroxybenzyl)-2-(3,4-dihydroxyphenyl)-2-hydroxyacetamide; and 2-(3,4-dihydroxyphenyl)-2-hydroxy-N-(3,4,5-trihydroxybenzyl)acetamide.

10. A cosmetic and/or pharmaceutical composition according to claim 9 comprising from 0.0001 to 30% by weight of said at least one of said hydroxymandelic acid amides of phenolic amines.

11. A sunscreen product comprising hydroxymandelic acid amides of phenolic amines, their stereoisomers or mixtures thereof, comprising the general formula (I)

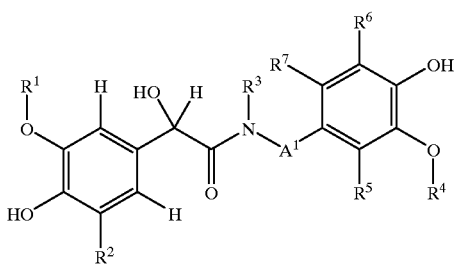

(I)

wherein

R$^1$ is a hydrogen atom or an alkyl radical having from 1 to 4 carbon atoms;

R$^2$ is a hydrogen atom or an —O—R$^8$ group, in which R$^8$ is a hydrogen atom or an alkyl radical having from 1 to 4 carbon atoms;

R$^3$ is a hydrogen atom, an acyl, alkyl or alkenyl radical having from 1 to 22 carbon atoms;

A$^1$ is a —CH$_2$— group or a —CH$_2$—CH$_2$— group;

R$^4$ is a hydrogen atom or an alkyl radical having from 1 to 4 carbon atoms; and R$^5$, R$^6$ and R$^7$ independently of one another are hydrogen atoms or —O—R$^9$ groups, where R$^9$ is a hydrogen atom or an alkyl radical having from 1 to 4 carbon atoms.

12. A food product comprising hydroxymandelic acid amides of phenolic amines, their stereoisomers or mixtures thereof, comprising the general formula (I)

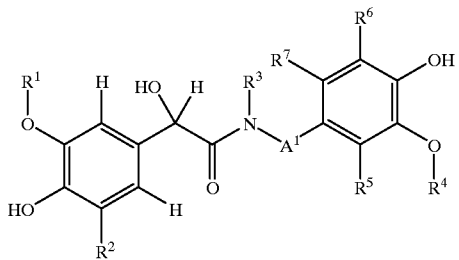

(I)

R$^1$ is a hydrogen atom or an alkyl radical having from 1 to 4 carbon atoms;

R$^2$ is a hydrogen atom or an —O—R$^8$ group, in which R$^8$ is a hydrogen atom or an alkyl radical having from 1 to 4 carbon atoms;

R$^3$ is a hydrogen atom, an acyl, alkyl or alkenyl radical having from 1 to 22 carbon atoms;

A$^1$ is a —CH$_2$— group or a —CH$_2$—CH$_2$— group;

R$^4$ is a hydrogen atom or an alkyl radical having from 1 to 4 carbon atoms; and R$^5$, R$^6$ and R$^7$ independently of one another are hydrogen atoms or —O—R$^9$ groups, where R$^9$ is a hydrogen atom or an alkyl radical having from 1 to 4 carbon atoms.

* * * * *